United States Patent [19]
Barra et al.

[11] Patent Number: 6,110,185
[45] Date of Patent: Aug. 29, 2000

[54] CANNULA HAVING INTEGRAL SUTURE TOURNIQUET

[75] Inventors: Jean-Aubert Barra, Brest, France; Philip T. Goforth, Grand Rapids, Mich.

[73] Assignee: Medtronic, Inc., Minneapolis, Minn.

[21] Appl. No.: 09/232,593

[22] Filed: Jan. 19, 1999

[51] Int. Cl.[7] .................................................. A61B 17/04
[52] U.S. Cl. ............................................................. 606/148
[58] Field of Search ................................... 606/139, 148, 606/108

[56] References Cited

U.S. PATENT DOCUMENTS

| | | | |
|---|---|---|---|
| 4,535,770 | 8/1985 | Lemole | 606/108 |
| 4,796,626 | 1/1989 | DeVries | 606/148 |
| 5,720,726 | 2/1998 | Marcadis et al. | 604/96 |

Primary Examiner—Michael Buiz
Assistant Examiner—Vy Q. Bui
Attorney, Agent, or Firm—Foley & Lardner

[57] ABSTRACT

A cannula having a main lumen extending therethrough is provided with a tourniquet integrally mounted to the cannula body. The tourniquet is positioned so that suture thread can be withdrawn therethrough and frictionally retained in place with respect to the cannula body. This structure is ideally suited for use in a cannula which is received in an incision surrounded by a purse string suture where the purse string suture is drawn tight to create a substantially fluid tight seal between the vessel wall and the cannula. The tourniquet lumens can be integrally molded with the cannula body or can be fixedly mounted thereto. In addition to the tourniquet, a pressure sensing lumen can similarly be integrated into the structure of the cannula body, depending upon the particular application of the cannula. This structure of the cannula is ideally suited for use as arterial cannulas, atrium cannulas and venous cannulas.

20 Claims, 2 Drawing Sheets

CANNULA HAVING INTEGRAL SUTURE TOURNIQUET

FIELD OF THE INVENTION

This invention relates to fluid cannulas and, more particularly, to fluid conveying cannulas having a suture tourniquet integrally formed or mounted thereto. The tourniquet according to the invention is particularly adapted for use in cardiovascular surgical applications.

BACKGROUND OF THE INVENTION

Fluid conveying cannulas have a wide variety of applications during invasive surgical operations. For example, coronary operations such as heart bypass surgery utilizes a venous cannula for removing oxygen depleted blood from the vascular system and arterial cannulas for returning oxygenated blood to the vascular system. Both venous and arterial cannulae are usually inserted through incisions cut into the right or left atrium, the vena cava oratium and aorta, respectively. Typically, the incision in which the cannula is inserted is surrounded by purse-string sutures which, when drawn tight around the inserted cannula will effectively prevent fluid from escaping the vessel.

Tourniquets are commonly used to contain the free ends of the suture thread. Typically, the tourniquets are free lengths of tubing through which the free ends of the suture thread are pulled through after creation of the purse-string suture. Once the purse-string suture has been drawn sufficiently tight around the inserted cannula, the free end of the suture thread is held in a fixed position with respect to the tourniquet by one of several conventional means such as wrapping the suture thread around a button, frictionally retaining the free end of the suture thread by inserting a cone-shaped plug into the end of the tourniquet or, alternatively, clamping the tourniquet closed around the suture thread by use of a conventional surgical clamp. Once the free ends of the suture threads have been sufficiently contained, then the tourniquet tubes are typically manually tied to the cannula to hold the sutures, tourniquet and cannula in place.

A recent development in cardiovascular surgical procedures is to conduct minimally invasive surgery which utilizes smaller apertures formed in the chest wall rather than cutting the sternum and spreading open the entire rib cage, as usually done in conventional open heart surgery. While there are many benefits being realized by minimally invasive surgical procedures, these procedures place many challenges on the surgeon as a result of the far smaller access aperture available to the surgeon as he or she performs the surgery. In view of the relative size of the access aperture, simplification of any and all equipment utilized in the surgical procedure can simplify these challenging procedures. The cannula having integral suture tourniquet takes less space in the surgical filed than a conventional cannula and thus it is particularly adapted for minimally invasive surgery.

SUMMARY OF THE INVENTION

The cannula according to the invention overcomes the problems of the prior art by fully integrating the suture tourniquet with the cannula thereby simplifying the equipment needed to perform surgical procedures.

In one aspect, the invention comprises an insertable surgical device configured to assist the user in creating a suture tourniquet around the device. The surgical device preferably comprises a cannula having opposed proximal and distal ends and a main lumen extending between the proximal and distal ends. At least one tourniquet is fixedly mounted to the cannula. The tourniquet has a proximal end, a distal end and a lumen extending between the proximal and distal ends. At least one suture retainer is provided on the surgical device and is configured to selectively hold a portion of suture thread to the surgical device.

Preferably, a pair of tourniquets are integrally molded into the cannula and the distal ends of the tourniquet are spaced a short distance approximately from the distal end of the cannula.

An alternative to integrally molding the tourniquets to the cannula would be to securely mount the tourniquets by other mechanical means such as adhesive, sonic welding, and the like.

In one embodiment, the suture retainer comprises a button provided adjacent the proximal end of the tourniquet. In practice, the suture thread is wrapped around the button and is frictionally retained thereon.

An alternative suture retainer is a plug configured to be telescopically received in the proximal end of the tourniquet lumen. When the plug is telescopically received in the proximal end of the tourniquet lumen, it is dimensioned to frictionally retain suture thread in the lumen.

In another aspect, the invention relates to a method of inserting a surgical device into a vessel. The method comprises providing a cannula substantially as described above and creating a purse-string suture in the vessel using conventional suture thread. The free end of the suture thread is pulled through the lumen of the tourniquet. Next, an incision is made in the vessel wall within the bounds of the purse-string suture. The distal end of the cannula is inserted into the incision and then the suture thread is quickly drawn tight by pulling the free end of the suture thread through the tourniquet lumen. Finally, the free end of the suture thread is fixed with respect to the cannula.

The surgical device can be removed by freeing the end of the suture thread from the suture retainer thereby releasing the purse-string suture. Next, the distal end of the cannula is withdrawn from the incision of the vessel.

BRIEF DESCRIPTION OF THE DRAWINGS

The invention will now be described with reference to the drawings in which.

DESCRIPTION OF THE PREFERRED EMBODIMENT

Figure 1:
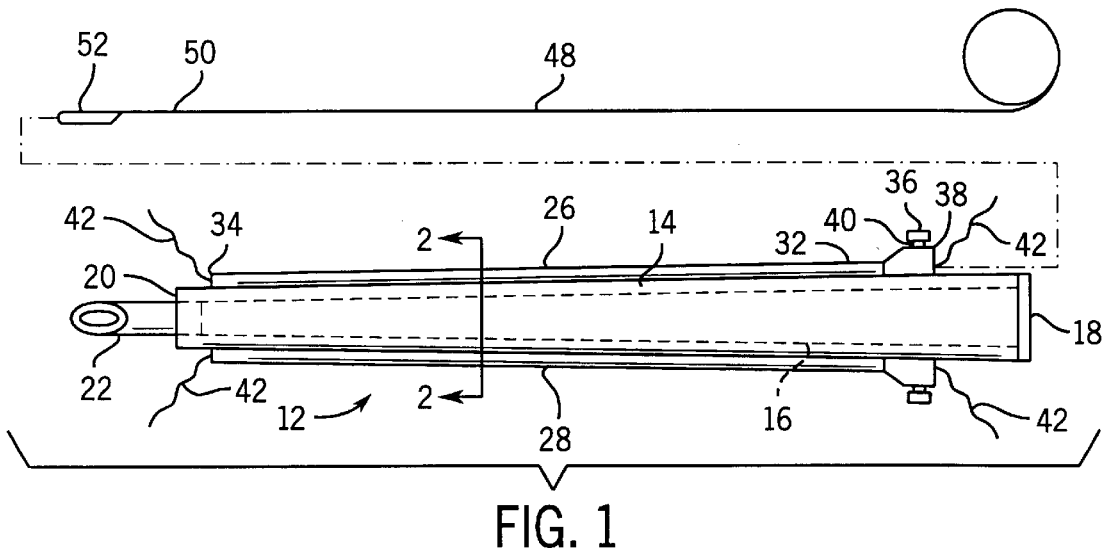
FIG. 1 is a plan view of a first embodiment of a cannula having integral tourniquet tubes according to the invention.
Figure 2:
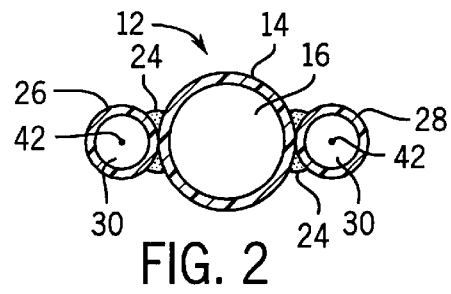
FIG. 2 is a cross-sectional view of the first embodiment of the cannula taken along lines 2—2 of FIG. 1.

Turning now to the drawings, and to FIGS. 1 and 2 in particular, a first embodiment of a cannula 12 according to the invention as shown. The cannula 12 comprises a cannula body 14 having a primary lumen 16 extending between the proximal 18 and distal ends 20. The cannula 12 as seen in FIG. 1 is an arterial cannula and therefore the proximal end 18 is adapted to be fluidly connected to the extracorporeal bypass circuit. The distal end 20 of the cannula has a discharge tip 22 securely mounted therein. In the preferred embodiment, the discharge tip 22 is preferably formed of plastic, but may also be formed of metal, and is curved to deflect the fluid flow therefrom substantially normal to the longitudinal axis of the lumen 16.

What distinguishes the structure of the arterial cannula seen in FIG. 1 from prior art is the integration of suture tourniquets into the cannula body. In the preferred embodiment, two tourniquets 26, 28 are mounted on opposite sides of the cannula body 14. In this embodiment the tourniquets 26, 28 are securely mounted to the exterior surface of the cannula body 14 by any medically approved adhesive 24. One example of a suitable adhesive includes ultraviolet curing adhesive. Alternatives to adhesive include solvent bonding and sonic welding.

The tourniquets are substantially identical and therefore only one tourniquet will be described in detail. The tourniquet 26 comprises a tourniquet lumen 30 extending from the proximal end 32 to the distal 34 of the tourniquet 26. Securely fastened to the proximal end 32 of the lumen 30 is a suture button 36 which extends outwardly from a button mounting 38. The button mounting 38 has a lumen (not shown) extended therethrough which is substantially contiguous with the tourniquet lumen 30. A shaft 40 extends between the suture button 36 and the button mounting 38.

In the preferred embodiment, the proximal end 32 of the tourniquet lumen 30 and the button mounting 38 are spaced a short distance from the distal end 20 of the cannula. Similarly, the distal end 34 of the tourniquet lumen 30 is spaced a short distance from the distal end of the cannula 22 to accommodate receipt of the suture thread 42.

The cannula having an integrated tourniquet according to the invention is ideally suited for use during minimally invasive cardiac surgical procedures. This surgical technique differs from the traditional open heart surgery primarily in the size of the openings that are formed in the chest wall. Under traditional open heart surgical procedures, the entirety of the chest cavity is opened by cutting through the sternum and spreading open the sternum and ribs to expose the entirety of the pericardium. In minimally invasive surgical procedures, much smaller apertures are cut into the chest wall to access only portions of the pericardium. For example, an aperture could be cut between two adjacent ribs or alternatively, a small portion of one rib could be removed to expose a portion of the pericardium. One inherent limitation upon the size of the aperture which needs to be formed in the chest wall is the size of the various cannulas and surgical tools which must pass through this aperture in order to complete the necessary surgical procedure. The cannula according to the invention is an improvement over the conventional cannula and tourniquet structures in that all of these various elements are integrated thereby simplifying the insertion and removal of surgical equipment through the chest wall resulting in more efficient use of the limited area of the chest wall aperture. practice, the surgeon creates a purse-string suture in the vessel, for example aorta, using conventional suture thread 42. After the purse-string suture has been created, the free ends of the suture thread 42 are captured in the hooked, distal end of a conventional wire thread retriever 48. First, the distal end 50 of the retriever 48 is telescopically received in the tourniquet lumen 30 so that the distal end 50 extends outwardly from the distal end of the lumen. The free end of the suture thread 42 is threaded through the hook 52 of the retriever and then the retriever 48 is withdrawn through the tourniquet lumen 30 pulling the suture thread 42 through the tourniquet lumen 30. At this point, the purse-string suture has been created, the free ends of the suture thread 42 have been pulled through the tourniquet lumens 30 and the discharge tip 22 of the cannula 12 is positioned immediately adjacent the wall of the vessel at the point of the purse string suture.

Next, the surgeon makes an incision in the vessel wall in the center of the purse string suture and thereafter immediately inserts the discharge tip 22 of the cannula 12 into the vessel through the incision. Next, the surgeon quickly draws tight the suture thread 42 by grasping the free end thereof and pulls tight the purse string suture around the distal end 20 of the cannula 12. Once sufficient tension has been created on the suture thread 42, the thread is wrapped around the shaft 40 of the suture button 36 a sufficient number of revolutions until the suture thread 42 is frictionally retained thereon. As long as the suture thread 42 remains around the suture button 36, a substantially fluid tight seal should remain in place between the vessel wall and the cannula 12.

When it is time to remove the cannula 12 from the vessel, the free end of the suture thread 42 is merely unwound from the suture button 36 thereby releasing the purse string suture. At this point, the cannula, in its entirety, can be withdrawn from the vessel leaving behind the suture thread 42. Finally, the suture is used to close the aortotomy.

Figure 3:
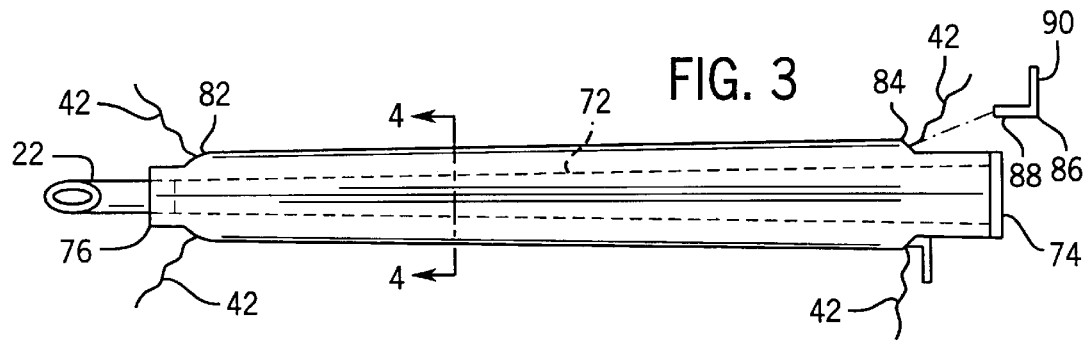
FIG. 3 is a plan view of a second embodiment of the cannula having integral tourniquet lumens according to the inventions.
Figure 4:
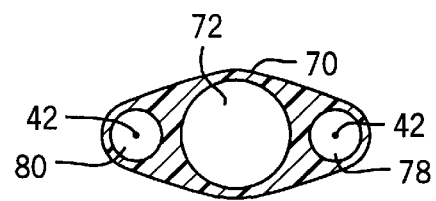
FIG. 4 is a cross-sectional view of the cannula taken along lines 4—4 of the FIG. 3.

A second embodiment of the cannula according to the invention is seen in FIGS. 3 and 4. Similar to the first embodiment, this embodiment is ideally suited for use as an arterial cannula. In this embodiment, the cannula 70 and tourniquets are integrally molded with one another. As seen in FIGS. 3 and 4, the cannula 70 is somewhat oval in cross section and has a main lumen 72 extending between the proximal 74 and the distal end 76 thereof. As in the first embodiment, a discharge tip 22 is securely mounted in the distal end 76. While the preferred embodiment utilizes a separately formed discharge tip, it is to be understood that the discharge tip could be integrally formed with the cannula body. Immediately adjacent the main lumen 72 are a pair of tourniquet lumens 78, 80. The tourniquet lumens 78, 80 have diameters sufficient to receive both the suture thread 42 and wire thread retriever 48 as discussed above. Similar to the first embodiment, the distal end 82 of the tourniquet lumen is positioned closely adjacent to the distal end 76 of the cannula 70. Preferably, the proximal end 84 of the tourniquet lumen 78 is spaced distally from the proximal end 74 of the cannula 72.

The second embodiment shows a second means for retaining the free end of the suture thread 42 in a fixed position. In this embodiment, a plug 86 is telescopically received in the proximal end of the tourniquet lumen 78. Preferably, the plug 86 has a conical shaped body 88 with a tab 90 provided at the terminal end thereof. The body 88 is dimensioned so that it tapers from a diameter which is less than the diameter of the tourniquet lumen to a diameter which exceeds that of the tourniquet lumen. With this configuration, the body 88 of the plug can be telescopically received in the tourniquet lumen after the free end of the suture thread 42 has been pulled therethrough. Properly designed, the friction between the thread 42, the plug 86 and the interior surface of the tourniquet lumen 78 will be sufficient to prevent movement of the suture thread 42 relative to the cannula 70.

Figure 5:
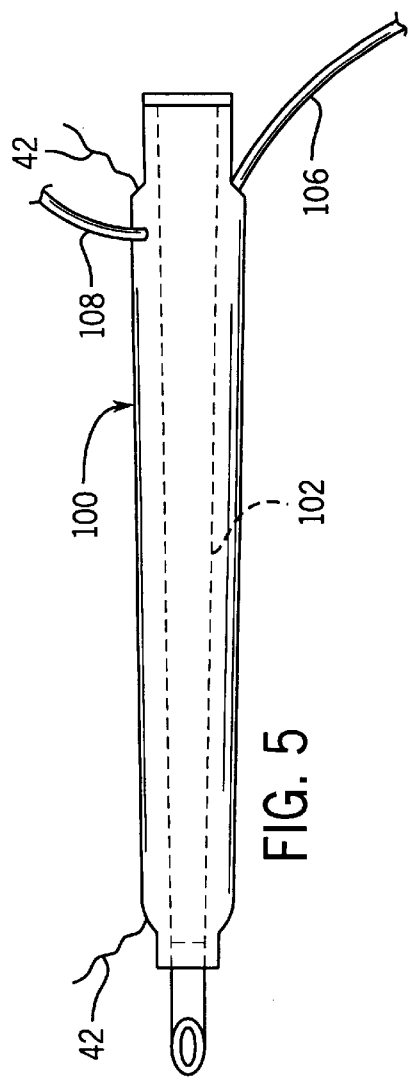
FIG. 5 is a plan view of a third embodiment of the cannula according to the invention.
Figure 6:
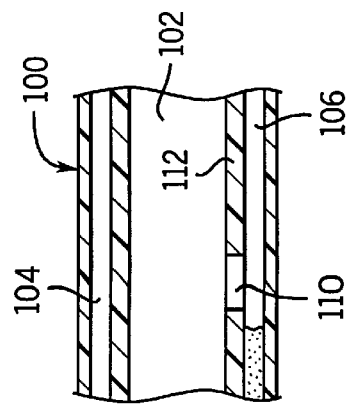
FIG. 6 is a longitudinal cross sectional view of a portion of the cannula see in FIG. 5.

FIG. 5 shows a third embodiment of a cannula having an integrated tourniquet according to the invention. Once again, this cannula is ideally suited for use as an arterial cannula. Similar to the second embodiment, this embodiment of the cannula 100 has a main lumen 102 and a pair of other lumens integrally formed therewith, namely a tourniquet lumen 104 and a pressure sensing lumen 106. The cross section of the cannula body is substantially identical to the cross section seen in FIG. 4, the only difference being that in this third embodiment one of the tourniquet lumens in FIG. 4 is utilized as a pressure sensing lumen 106.

Similar to the second embodiment, the proximal and distal ends of the tourniquet lumen 104 is dimensioned to accommodate and receive the suture thread 42 therethrough. In this embodiment, still yet another means for retaining the suture thread 42 in a fixed position relative to the cannula 100 as shown. In this embodiment, the tourniquet lumen 104 is clamped shut by the opposed tips of a conventional surgical clamp 108. After the free end of the suture thread 42 has been pulled through the tourniquet lumen 104 and the thread has been pulled taut to seal the purse string suture, then the opposed tines of the conventional surgical clamp grasp the cannula 100 on opposite sides of the tourniquet lumen 104 and are squeezed against one another to frictionally retain the suture thread therein.

One of the tourniquet lumens in this embodiment has been replaced by a pressure sensing lumen 106. In this embodiment, the pressure sensing lumen 106 extends outwardly from the cannula a short distance to be mounted to conventional pressure sensing equipment. The purpose of the pressure sensing lumen and sensing equipment is to evaluate the pressure of the fluid passing through the main lumen 102 of the cannula. In order to accomplish this, a small fluid aperture 110 is cut in the web 112 separating the pressure sensing lumen 106 from the main lumen 102. The pressure sensing lumen 106 is fluidly sealed distally of the fluid aperture 110 by inserting an acceptable adhesive or other suitable compound in the distal end of the lumen. With this structure, the pressure sensing equipment which is mounted to the proximal end of the pressure sensing lumen 106 can effectively monitor the pressure of the fluid flowing through the main lumen 102. All of this is accomplished with the ease and simplicity of the integral tourniquet as described above.

The preferred form of the cannula incorporating the pressure sensing lumen utilizes a single tourniquet lumen, however, it is to be understood that more than one tourniquet lumen could be incorporated into this particular embodiment of the cannula 100 depending upon the requirements for the particular application of the cannula 100. The additional lumens could merely be spaced around the periphery of the main lumen 102.

Figure 7:
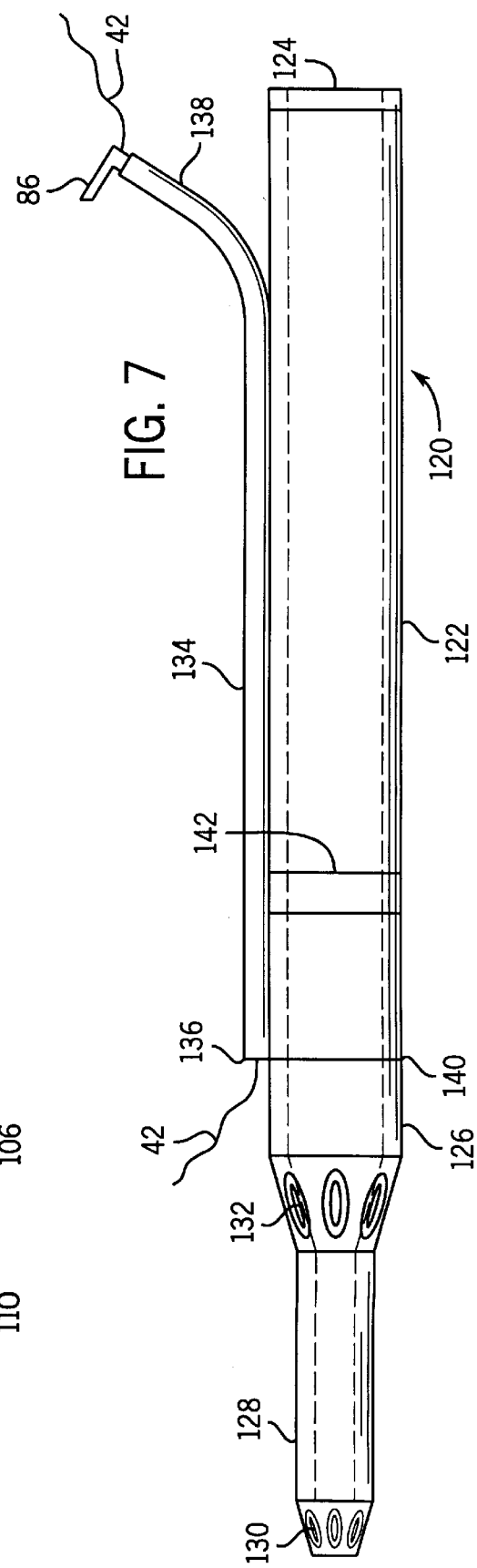
FIG. 7 is a plan view of a fourth embodiment of the cannula according to the invention.

All of the embodiments of the cannula reviewed above are ideally suited for use as arterial cannulas. FIG. 7 depicts still yet another embodiment of the cannula having an integrated tourniquet according to invention. In this embodiment, the cannula is ideally suited for use as a venous cannula for use in a coronary operation. In this embodiment, the cannula 120 comprises a cannula body 122 having a proximal end 124 and a distal end 126. The proximal end 124 is adapted to be fluidly connected to the extracorporeal bypass circuit and the distal end 126 is adapted to be received in the vena cava. A two stage tip 128 is provided at the distal end 126 of the cannula body. The particular structure and configuration of the two stage tip is described more completely in U.S. Pat. No. 4,129,129 which is expressly incorporated herein by reference. The two stage tip 128 has a first set of fluid apertures 130 provided at the distal end of the tip and a second set of apertures 132 which are spaced proximally from the first set 130.

Similar to the third embodiment as seen in FIG. 5, the preferred form of the venous cannula utilizes only a single tourniquet 134. Similar to the first embodiment, this tourniquet 134 is secured to the exterior surface of the cannula body 122 by a suitable adhesive as described above. The distal end 136 of the tourniquet is spaced a prescribed distance from the second set of fluid apertures 132. In this embodiment, the proximal end 138 of the tourniquet 134 is not adhered to the cannula body. In other words, this portion of the tourniquet 134 can be manipulated and deflected away from the cannula body. Depending upon the application, it may be easier for the surgeon to set the free end of the suture thread 42 in the tourniquet if the distal end of the tourniquet 136 can be manipulated a short distance independently from the cannula body 122. In this embodiment, the free end of the suture thread 42 is frictionally retained in the tourniquet by a plug 86 as described above.

Another feature incorporated into the fourth embodiment of the cannula 120 are insertion markings 140, 142. These markings are provided on the exterior surface of the cannula body 122 and are plainly visible by the surgeon. These markings help to guide the surgeon in properly positioning the cannula in the vena cava.

Each of the several embodiments incorporate a variety of different features. It is to be understood that the features and structures depicted in the various embodiments can be interchanged depending upon the particular application. For example, the venous cannula depicted in FIG. 7 can be integrally molded similar to the structure seen in the second embodiment of FIGS. 3 and 4. A person skilled in the art can easily appreciate the various combinations of the structural features embodied in the various embodiments.

The discussion of the various embodiments of the cannula according to invention have focused on application as arterial and venous cannula. While the structure of the invention is ideally suited for these particular applications, it is to be understood that this particular invention is not limited to arterial or venous cannulas. Rather, any cannula which is inserted through an incision or other aperture and which must be retained in this position by suture thread is clearly within the scope of this invention.

What is claimed is:

1. An insertable surgical device configured to assist a user in creating a suture thread tourniquet around the surgical device, the surgical device comprising:

a cannula having a proximal end, a distal end and a main lumen extending at least partially through the length of the cannula;

at least one tourniquet having a proximal end, a distal end and a tourniquet lumen extending therethrough, the tourniquet being integrated with the cannula and extending at least partially along the length of the cannula, the at least one tourniquet lumen being adapted to receive suture thread and;

at least one suture retainer configured to selectively hold a portion of the suture thread to the surgical device.

2. The insertable surgical device of claim 1, wherein the surgical device has two tourniquets integrated with the cannula.

3. The insertable surgical device of claim 2, wherein the two tourniquets are diametrically opposed with respect to the cannula.

4. The insertable surgical device of claim 2, wherein the two tourniquets are integrated with the cannula by an adhesive.

5. The insertable surgical device of claim 2, wherein the two tourniquet lumens are integrally molded with the cannula.

6. The insertable surgical device of claim 1 wherein the at least one suture retainer comprises:
   a button mounting, having a button mounting lumen extending therethrough, the button mounting lumen being substantially coaxially aligned with the at least one tourniquet lumen; and
   a suture button extending from the button mounting.

7. The insertable surgical device of claim 1 wherein the at least one suture retainer comprises:
   a plug configured to be telescopically received in the proximal end of the tourniquet lumen and adapted to frictionally retain the suture.

8. The insertable surgical device of claim 7 wherein the plug has a tab extending from the plug configured to facilitate insertion and removal from the proximal end of the tourniquet lumen.

9. The insertable surgical device of claim 1 further comprising:
   a pressure sensing lumen, the pressure sensing lumen being mounted to the cannula, and fluidly interconnected with the main lumen of the cannula.

10. The insertable surgical device of claim 1, wherein the cannula comprises:
    a first fluid aperture provided adjacent the proximal end of the cannula; and
    a second fluid aperture spaced distally from the first fluid aperture and intermediate the proximal and distal ends of the cannula.

11. The insertable surgical device of claim 1 wherein the cannula has at least one insertion marking provided on the cannula to assist proper insertion of the surgical device.

12. An improved cannula having a proximal end, a distal end and a main lumen extending between the proximal and distal ends, the improvement comprising:
    at least one tourniquet integrally molded into the cannula so that it extends along the length of at least a portion of the cannula, the at least one tourniquet having a proximal end, a distal end and a lumen extending through at least a portion thereof, the lumen of the at least one tourniquet being adapted to telescopically receive suture thread therethrough and the distal end of the tourniquet lumen being spaced proximally from the distal end of the cannula.

13. An improved cannula according to claim 12 wherein two tourniquet lumens are integrally molded into the cannula and are diametrically opposed to one another.

14. An improved cannula according to claim 12 and further comprising a pressure sensing lumen provided in the cannula and being fluidly connected to the main lumen of the cannula.

15. An improved cannula according to claim 12 and further comprising a suture thread retainer comprising:
    a suture button provided adjacent the proximal end of the tourniquet lumen, the button being adapted to have suture thread wrapped thereabout and to frictionally retain the suture thread thereon.

16. An improved cannula according to claim 12 and further comprising a suture thread retainer comprising:
    a plug configured to be telescopically received in the proximal end of the tourniquet lumen and adapted to frictionally retain suture thread in the lumen.

17. A method of inserting a surgical device into a vessel, the method comprising:
    providing a surgical device having a cannula with a first end and a second end, at least one tourniquet lumen integrated with the cannula, and at least one suture retainer;
    creating a purse-string suture in the vessel using a suture thread, the suture thread having at least one free end;
    pulling the at least one free end of the suture thread through the at least one tourniquet lumen;
    making an incision in the vessel within the bounds of the purse-string suture;
    inserting the first end of the cannula into the incision;
    drawing tight the suture thread by pulling the at least one free end; and
    fixing the at least one free end of the suture thread substantially in place by utilizing the suture retainer.

18. The method of claim 17 further comprising the steps of:
    providing a wire thread retriever having a hook on one end thereof, the retriever being adapted to be telescopically received in the tourniquet lumen; and
    catching the at least one free end of the suture thread in a wire thread retriever hook prior to the step of pulling the at least one free end of the suture thread.

19. The method of claim 17 wherein the suture retainer includes a suture button and the fixing step includes wrapping the at least one free end of the suture thread around the suture button.

20. The method of claim 17 wherein the suture retainer includes a plug and the fixing step includes positioning the plug in the tourniquet lumen to frictionally retain the suture thread.

* * * * *